United States Patent
Hu

(10) Patent No.: US 9,681,620 B2
(45) Date of Patent: Jun. 20, 2017

(54) BARLEY MUTANT LINES HAVING GRAIN WITH ULTRA-HIGH BETA GLUCAN CONTENT

(71) Applicant: The United States of America, as represented by the Secretary of Agriculture, Washington, DC (US)

(72) Inventor: Gongshe Hu, Pocatello, ID (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 252 days.

(21) Appl. No.: 14/249,584

(22) Filed: Apr. 10, 2014

(65) Prior Publication Data
US 2015/0289466 A1    Oct. 15, 2015

(51) Int. Cl.
*A01H 5/10*    (2006.01)

(52) U.S. Cl.
CPC ..................... *A01H 5/10* (2013.01)

(58) Field of Classification Search
None
See application file for complete search history.

(56) References Cited

U.S. PATENT DOCUMENTS

2012/0129805 A1* 5/2012 Li ..................... A01H 5/10
514/60

OTHER PUBLICATIONS

Munck et al, 2004, Journal of Cereal Science, 40:213-222.*
Islamoyic et al, 2013, Mol. Breeding., 31:15-25.*
Obert et al 2008, J. of Plant Registration, 2:10.*
El Khoury, D. et al., "Beta Glucan: Health Benefits in Obesity and Metabolic Syndrome", (2012) Journal of Nutrition and Metabolism 2012:1-28.
Hodgdon et al., "Azide Mutagenesis—varietal response, pregermination conditions and concentration", (1979) Barley Genetics Newsletter 9:1-4.
Munck, L. et al., "Near infrared spectra indicate specific mutant endosperm genes and reveal a new mechanism for substituting starch with (1->3,1 ->4)-Beta-glucan in barley" (2004) Journal of Cereal Science 40:213-222.

* cited by examiner

*Primary Examiner* — Jason Deveau Rosen
(74) *Attorney, Agent, or Firm* — John D. Fado; David L. Marks

(57) ABSTRACT

The present disclosure relates to barley plants having grain with ultra-high beta-glucan content, methods for constructing said barley plants, grain therefrom and uses thereof. In an exemplary embodiment, present disclosure provides a barley plant having grain with ultra-high beta-glucan content known as CM1.

10 Claims, No Drawings

BARLEY MUTANT LINES HAVING GRAIN WITH ULTRA-HIGH BETA GLUCAN CONTENT

FIELD OF THE INVENTION

The invention relates to barley cultivars having grain with ultra-high beta glucan content and uses thereof.

BACKGROUND OF THE INVENTION

Barley is one of the world's most important cereal crops. In addition to containing eight essential amino acids, antioxidants, vitamins and minerals essential to health, barley is also high in dietary fiber.

Beta-glucans (β-glucans) are an important component of the dietary fiber present in barley. β-glucan has many known health benefits and thus, the inclusion of barley in the diet can have many beneficial effects. Indeed, eating whole-grain barley has been shown to help regulate blood sugar and eating barley also helps to lower cholesterol levels, reduces visceral fat and lowers the incidence of heart disease (see e.g., Nilsson, A.; et al. (2006) European Journal of Clinical Nutrition 60 (9): 1092-1099; Pick M, et al. (1998) Int J Food Sci Nutr. 49(1):71-78; Zeković D B, et al. Critical Reviews in Biotechnology. 2005; 25(4):205-230; Jue Li, et al. Nutrition—November 2004 (Vol. 20, Issue 11, Pages 1003-1007, Abumweis S S, et al. European Journal of Clinical Nutrition. 2010; 64(12):1472-1480; Choi J S, et al. Molecular nutrition & food research. 2010 July; 54(7):1004-1013; D. El Khoury, et al. J Nutr Metab. 2012; 2012; Carlo Agostoni et al. EFSA Journal 2011; 9(12):2471; Shimizu, C. et al. Plant Foods and Human Nutrition, March 2008; 63(1):21-5).

Given the health benefits of β-glucan consumption, a barley cultivar having grain with ultra-high beta-glucan content is highly desirable.

Fortunately, as will be clear from the following disclosure, the present invention provides for these and other needs.

SUMMARY OF THE INVENTION

In exemplary embodiments, the disclosure provides barley plants having grain with ultra-high beta-glucan content, a seed thereof, tissue culture of regenerable cells therefrom, and/or a protoplast produced from the tissue culture. In one exemplary embodiment, the disclosure provides a barley plant having grain with ultra-high beta-glucan content, or a part thereof, produced by growing the seed.

In some exemplary embodiments, the disclosure provides a barley plant having grain with ultra-high beta-glucan content, or a part thereof, having all the physiological and morphological characteristics of the CM1, representative seed of such line having been deposited with the American Type Culture Collection on May 17, 2012 and having been assigned ATCC accession No. PTA-12911, a seed thereof, a tissue culture of regenerable cells produced therefrom and/or protoplast produced from the tissue culture of regenerable cells.

In other exemplary embodiments, the disclosure provides a hybrid barley plant, wherein the lineage of at least one parent plant comprises a barley plant having grain with ultra-high beta-glucan content, having all the physiological and morphological characteristics of the variety CM1, representative seed of such line having been deposited with the American Type Culture collection on May 17, 2012 and having been assigned ATCC accession No. PTA-12911. In some exemplary embodiments, the disclosure provides grain from the hybrid barley plant wherein the grain has ultra-high beta-glucan content. In one exemplary embodiment, the at least one parent plant of a hybrid barley plant is the barley plant CM1, representative seed of such line having been deposited with the American Type Culture collection on May 17, 2012 and having been assigned ATCC accession No. PTA-12911. In another exemplary embodiment, the at least one parent plant, CM1, is crossed to a second parent plant, wherein the second parent plant is "Tetonia" and wherein the hybrid barley plant has grain with ultra-high beta-glucan content. In one exemplary embodiment, the hybrid barley plant from a cross between CM1 and "Tetonia" is a member selected from the group consisting of 10ARS313-791, 10ARS313-930, 10ARS313-854, 10ARS313-924, 10ARS313-963, 10ARS313-355, 10ARS313-782, 10ARS313-777, 10ARS313-575, 10ARS313-418, 10ARS313-428, 10ARS313-831 and 10ARS313-849.

In still other exemplary embodiments, the disclosure provides a barley plant having grain with ultra-high beta-glucan content of the variety CM1, representative seed of such line having been deposited with the American Type Culture collection on May 17, 2012 and having been assigned ATCC accession No. PTA-12911, or a selfed progeny thereof or an F1 hybrid thereof wherein the barley plant has grain with ultra-high beta-glucan content.

In still other exemplary embodiments, the disclosure provides grain from a barley plant known as CM1, representative seed of such line having been deposited with the American Type Culture collection on May 17, 2012 and having been assigned ATCC accession No. PTA-12911 or a progeny thereof.

Other features, objects and advantages of the invention will be apparent from the detailed description which follows.

DETAILED DESCRIPTION OF THE INVENTION

Definitions

The term "plant" as used herein refers to whole plants, plant bodies, plant organs (e.g., leaves, stems, flowers, roots, etc.), seeds, plant tissues, plant cells and progeny of same. In an exemplary embodiment, a plant cell includes callus. In another exemplary embodiment, a plant organ includes a root, a leaf, a flower and/or the like. The term "plant" refers to plants of any variety of ploidy levels, including polyploid, diploid, haploid and hemizygous.

The term "barley plant having grain with ultra-high beta-glucan content" as used herein, refers to a barley plant (*Hordeum vulgare.* L) which produces grain that has a beta-glucan content of greater than about 13% beta-glucan by dry weight. Typically, a "barley plant having grain with ultra-high beta-glucan content" has a beta glucan content that is in a range that is between about 14% to about 19% by dry weight. An exemplary "barley plant having grain with ultra-high beta-glucan content" is CM1.

The term "beta glucan" or β-glucan as used herein, refers to non-starch polysaccharides of D-glucose monomers comprising β-(1,4)-linked glucose units separated every 2-3 units by β-(1,3)-linked glucose.

The term "grain" or any grammatically equivalent expression as used herein, refers to grain kernels from a barley plant. In some exemplary embodiments, the term "grain"

refers to grain kernels from a barley plant having grain with ultra-high beta-glucan content.

The term "cross" or "crossing" as used herein refers to a simple X by Y cross, or the process of backcrossing, depending on the context.

The term "backcross" as used herein refers to a process in which a breeder crosses a hybrid progeny line back to one of the parental genotypes one or more times.

I. Introduction

In an exemplary embodiment, the invention provides a barley cultivar having grain with ultra-high beta-glucan content.

β-glucans have known health benefits (see e.g., Food and Drug Administration: FDA (2006) Food Labeling: 'Health claims: Soluble dietary fiber from certain foods and coronary heart disease'. In: Code of Federal Regulation Title 21 Part 101) and barley is known to have more β-glucan content than any other grain. Despite the relatively high beta-glucan content, there is an upper limit of about 8.5% β-glucan content in the known barley cultivars with some variation due to growing conditions (see e.g., Izydorczyk M S, et al. J Agric Food Chem. 2000 April; 48(4):982-9; Holtekjølen A K, et al. Food Chemistry. 2006; 94(3):348-358; Hang, A., et al. (2007) Crop Sci. 47: 1754-1760).

Given the health benefits of β-glucan consumption and overall value of barley as health food, it would be of great benefit to have available barley cultivars having the highest possible β-glucan content. Fortunately, the variety CM1 disclosed herein below is a barley cultivar having ultra-high beta glucan content.

II. Mutagenesis and Selection to Produce a Barley Plant Having Ultra-High Beta-Glucan Content.

A. General Methods

Methods disclosed herein utilize routine techniques in the field of barley genetics and cultivation. Basic terminology in the field of genetics and cytogenetics can be found e.g., In: Robert C. King, William D. Stansfield, *A Dictionary of Genetics*, sixth edition 2002, Oxford University Press; basic texts in barley genetics and cultivation include, e.g., *Barley Science: Recent Advances from Molecular Biology to Agronomy of Yield and Quality*, Gustavo A Slafer, Jose Luis Molina-Cano, Roxana Savin, Jose Luis Araus and Ignacio Romagosa eds; CRC Press, Mar. 12, 2002-665 pages and *Barley: Genetics, Biochemistry, Molecular Biology and Biotechnology*, Peter R. Shewry ed. Oxford University Press, USA (1992).

B. Mutagenisis of Barley

Induced mutations have been extensively used to improve main crop species, including cereals such as barley (*Hordeum vulgare* L). See e.g., A. R. Prina, E. A. Favret (2008) Hereditas 98(1):89-94. Sodium azide is typically used in a wide range of concentrations for barley mutagenesis (e.g., $10^{-5}$ to $10^{-2}$ M, see e.g., Hodgdon et al, 1979 Barley Genetics Newsletter, Vol. 9: 29-33). As is known in the art, mutation frequencies positively correlate with the concentrations of the chemical used. However, higher concentrations may have lethal effect on seed germination.

In exemplary embodiments, the concentration of sodium azide used for mutagenesis of barley as disclosed herein is in a range that is between about 1 mM and about 2 mM.

C. Selection of Mutants Having High Beta-Glucan Content

In exemplary embodiments, barley plants having grain with ultra-high beta-glucan content are selected by screening plants grown from mutagenized seed for a beta-glucan content that is at least about 30% greater than the beta-glucan content of the corresponding parent plant. Thus, in some exemplary embodiments, barley plants having ultra-high beta-glucan content are barley plants grown from mutagenized seed which have beta-glucan content that is at least about 30% greater that the beta-glucan content of the parent plant.

In other exemplary embodiments, barley plants having grain with ultra-high beta-glucan content are selected by screening plants grown from mutagenized seed for a beta-glucan content that is at least about 40% greater than the beta-glucan content of the corresponding parent plant. In still other exemplary embodiments, barley plants having grain with ultra-high beta-glucan content are selected by screening plants grown from mutagenized seed for a beta-glucan content that is at least about 50% greater, at least about 60% greater, at least about 70% greater, at least about 80% greater, at least about 90% greater, at least about 100% greater, at least about 110% greater, at least about 120% greater, at least about 130% greater, at least about 140% greater, at least about 150% greater, at least about 175% greater, at least about 200% greater, at least about 250% greater, at least about 300% greater, than the beta-glucan content of the corresponding parent plant.

III. Measuring Beta-Glucan Content

In general, beta-glucan content is measured using any method known in the art. In some exemplary embodiments, beta-glucan is determined using e.g., AACC International Approved Method 32-23; a Megazyme mixed-linkage β-glucan assay kit (Megazyme International Ireland Ltd., Bray Business Park, Bray, Co. Wicklow, Ireland), etc. In one exemplary embodiment, beta-glucan content is measured according to the method of Hu and Barton 2008 (Gongshe Hu and Charlotte Burton (2008) Cereal Chemistry 85: 648-653, which is incorporated herein by reference).

IV. Measuring Fiber and Vitamin E Content

In general, total fiber and soluble fiber are measured by any method known in the art e.g., AACC International Approved Methods-AACC Method 32-05.01. Total Dietary Fiber; AACC International Approved Methods-AACC Method 32-07.01. Soluble, Insoluble, and Total Dietary Fiber in Foods and Food Products AACC International Approved Methods-AACC Method 32-07.01. Soluble, Insoluble, and Total Dietary Fiber in Foods and Food Products.

IV. Uses for Barley Plant Having Ultra-High Beta-Glucan Content

A. Use in Breeding Programs

In exemplary embodiments, a barley plant having grain with ultra-high beta glucan content is used in barley breeding programs to provide hybrid barley plants having grain with ultra-high beta-glucan content. In some exemplary embodiments, at least one parent plant in a cross to provide hybrid barley plants having grain with ultra-high beta-glucan content is the variety CM1 representative seed of which has been deposited with the American Type Culture Collection (ATCC), Patent Depository, on May 17, 2012 and which has the ATCC accession number is PTA-12911 (See section V. hereinbelow). In other exemplary embodiments, at least one parent plant in a cross to provide hybrid barley plants having grain with ultra-high beta-glucan content is the variety CM1 and the CM1 parent is crossed to a second barley plant that is not CM1. The second barley plant can be any barley plant. In some exemplary embodiments, the second barley is the variety "Tetonia" (see e.g., D. E. Obert et al. Registration of 'Tetonia' Barley Journal of Plant Registrations (2008) Vol. 2 No. 1, p. 10-11). In other exemplary embodiments, the second barley plant is "Transit" (see e.g., Obert D E, Hang A, Hu G, Burton C, Saterfield K, Evens C P, Marshall J M, and Jackson E W. 2011. Registration of 'Transit' High β-Glucan Spring Barley. Journal of Plant Registrations 5: 270-272).

B. Use in Food Production

Processed barley grain products are used as components of consumer products in the form of thickeners, binders or extenders. Thus, in some exemplary embodiments, a barley plant having grain with ultra-high beta-glucan content is used to produce food products and/or nutritional supplements.

Barley having grain with ultra-high beta-glucan content is processed for human and/or animal consumption by any method known in the art (see e.g., Barley for Food and Health: Science, Technology, and Products, Rosemary K. Newman, C. Walter Newman 2008, 246 pgs.; Wheat, Rice, Corn Oat Barley and Sorghum Processing Handbook (Cereal Food Technology) by NIIR BOARD OF CONSULTANTS & ENGINEERS (2006))

V. Deposit Information

A deposit of a barley plant having ultra-high beta-glucan content, CM1, disclosed hereinbelow and recited in the appended claims has been made with the American Type Culture Collection (ATCC), Patent Depository, 10801 University Blvd., Manassas, Va. 20110, U.S.A. The date of deposit was May 17, 2012. All restrictions upon the deposit have been removed, and the deposit is intended to meet all of the requirements of 37 C.F.R. 1.801-1.809. The ATCC accession number is PTA-12911. The material description is: Barley (*Hordeum valgare*) seeds: CM1. The deposit will be maintained in the depository for a period of 30 years, or 5 years after the last request, or for the effective life of the patent, whichever is longer, and will be replaced as necessary during that period.

The following examples are offered to illustrate, but not to limit the invention.

EXAMPLES

Example 1

The following example illustrates construction and testing of a barley plant having grain with ultra-high beta-glucan content. In particular the following Example illustrates construction of the line known as: CM1, which was deposited with the American type Culture Collection on (May 17, 2012), and which has been assigned ATCC accession number PTA-12911.

Ultra-high beta-glucan barley lines were created by chemical mutagenesis using sodium azide. Seed from four known barley lines, CDC Alamo (see e.g., Rossnagel et al. (1999) "*CDC Alamo 2-Row Hulless Zero Amylose Barley*" Barley Newsletter, Vol. 43), Waxbar, Baronesses, and 03AH 2229, were treated with sodium azide at a concentration of sodium azide at 1 mM.

The Waxbar variety was protected with a Plant Variety Protection Certificate in 1988 under the PV number of 8800084 in PVPO list of U.S. protected Varieties. The Certificate is now expired. The major character of the Waxbar is the amylose-free hulless spring variety.

Baronesses is a 2-row feed barley developed in Germany and seeds are produced by the Western Plant Breeders company in the United States. It is still a protected variety in US under the PV number of 9300211. The major character of this cultivar is high yield. It has been used as control in the yield trials.

03AH2229 is a line developed in the local research program in Aberdeen, Idaho. 03AH2229 is a 2-row hulless spring barley line derived from the cross between Azhul and Thuringa. It has beta-glucan at about 8-9% but yield is low (see e.g., Agronomic Performance of Food Barley at Pendleton and Moro Steve Petrie, et al. (2007) Agricultural Experiment Station, Oregon State University Special Report 1074 June 2007). 03AH2229 was chosen based on the assumption that it is better adaption to the climate condition in southeast Idaho region. This mutagenized population has not been used for high beta-glucan mutation screening yet.

Mutagenisis of the above disclosed barley varieties was mutagenized according to the following method:

Mutagenesis Method

1. Cold Soak seed (500 g-1000 g) in 5 L tap water (use 6 L Flask) for 16 Hours in 0 to 4° C.
2. Rinse seed with 5 L 20° C. tap water for 4 times
3. Soak seed in 5 L tap water for 4 hours at 20° C.
4. Rinse seed with deionized (distilled will work) water for 4 times
5. Fill Flask or beaker with 4.5 L deionized water
6. Add 0.5 L 1 M KH2PO4 (pH=3.0), swirl to mix
7. Go to the fume hood to add 5.0 mL 1 M NaN3 (in distilled water), mix thoroughly
8. Connect aeration system to flask for 2 hours. Swirl every 0.5 hours. Pull tired bags every 15 min. if using beaker.
9. Remove solution and rinse the seeds for 3 times in tap water
10. Wash seeds for 0.5 hour in running water
11. Dry seeds on paper towel in fume hood overnight
12. Planting or store in paper bag up to 2 weeks After Sodium Azide treatment, the seeds (called M0 seeds) were planted in the field in Aberdeen in 2006 spring. Individual plants were harvested separately. Two seeds from each harvested plant were collected. Those seeds (called M1 seeds) were pooled together for the same barley line. So, total four pools of M1 seeds were obtained for CDC Alamo, Waxbar, Baronesse, and 03AH2229, respectively.

The M1 seeds were planted in the field in Aberdeen in the spring of 2007, plants were harvested and threshed individually. The cleaned seeds from this generation (called M2 seeds) was subjected for beta-glucan measurement. The lines with significant changes of beta-glucan content compared to their corresponding wild-type lines were selected as the candidate mutants.

The criteria for selecting the mutant candidate was that the changes of beta-glucan content from grains was at least 30% compared to the wild-types.

About 4000 M2 seeds from each family were screened from CDC Alamo, Waxbar, and Baronesses. A particular mutation called CM1 was identified from the mutagenized population of CDC Alamo line in 2007.

The forth population of 03AH2229 has not been screened for beta-glucan mutant yet.

Characterization of the CM1 Mutant

CM1 was first noticed by its extreme high beta-glucan content in the M2 seeds screening. To confirm the significant changes of beta-glucan, CM1 was planted in greenhouse in 2007 winter, in Aberdeen field in 2008, and greenhouse in 2009 winter, grains of CM1 from those plants in different growth conditions were measured for beta-glucan contents and compared to the wild-type plants in the same growth conditions. All the tests confirmed that CM1 was consistently 100% more in beta-glucan content than that in the wild-type.

The ranges of the beta-glucan content in CM1 grains are 14% to 18% at dry matter based. In general, as is known in the art, beta glucan content may vary to some extent with the growth conditions. Environmental factors such as e.g., water and nitrogen supply during the seed development stage can affect beta glucan content. Typically, dry conditions enhance beta-glucan content in grains and nitrogen decreases the beta-glucan content. Thus, the beta-glucan content of the same barley line can vary somewhat in different locations and years.

To evaluate the beta-glucan content in CM1 more precisely, we developed near iso-genic lines. The near isogenic lines were developed by crossing CM1 to its wild-type parental line of CDC Alamo in 2007. F1 seeds were planted in greenhouse and F2 seeds were planted in 2008 in the Aberdeen field with both parents as controls. Four F3 plants with the same beta-glucan contents of CM1 were pooled together to represent the mutant near iso-genic line while the four plants with the similar wild-type CDC Alamo beta-glucan content were pooled together to represent the wild-type near isogenic line. Those near iso-genic lines were then used in planting and testing for fiber compositions of the grains. Comparing to the corresponding wild-type near isogenic lines which has 7.2-8.5% of beta-glucan, CM1 has about 100% increased in beta-glucan in grains. Data is shown in Table 1. Beta-glucan content was measured using methods known in the art (Hu and Burton, Cereal Chemistry 85: 648-653).

The CM1 mutant was further characterized for total fiber as well as for the water extractable fibers of arabinoxylan and glucomann using methods known in the art (Total Dietary Fiber: The MegaZyme Kit for total dietary fiber (K-TDFR from MegaZyme International, Ireland) was used. Performance of the assay was followed the instructions from the manufacture. Glucomann content in grains: The MegaZyme Kit K-GLUM (MegaZyme International, Ireland) was used. Performance of the assay was followed the instructions from the manufacture. Arabinoxylan content in grains: The MegaZyme Kit K-GLUM (MegaZyme International, Ireland) was used. Performance of the assay was followed the instructions from the manufacture.

Characterization of the CM1 mutant by measurements of other fibers in the grains revealed that other water extractable fibers of arabinoxylan and glucomann are also increased by 53% and 50%, respectively, compared the wild-type parental CDC Alamo. CDC Alamo is the parental line of CM1. Total fiber of CM1 grains is increased by 66%. Seeds look thinner, but plants showed normal biological characters in terms of seed germination, plant height, leaf color and size, heading dates, flower development, and seed set.

The high fibers in CM1 make it a valuable material for food industry. Fibers and Vitamin E contents are associated with the high beta-glucan content because the near iso-genic lines were used for those tests.

In addition to the high fiber content, CM1 mutant also showed Vitamin E content that was higher than that in the corresponding wild-type. Vitamin E was measured by methods known in the art (see Jackson et al, (2008) Crop Sci. 48:2141-2152) by Dr. Mitchell Wise lab in USDA-ARS, Madison, Wis.

Content of total tocol is 110 mg/Kg in CM1 compared to the 76 mg/Kg in the wild-type. The increase is about 45%. Since Vitamin E is related to the anti-oxidation, the CM1 may potentially provide some stress tolerance for the plants and extending the shelf-life for the food products.

The experimental data for this mutant is summarized in Table 1.

More importantly CM1 does not have clear negative impact on plant biological traits in field based on the eyeball observation and some data collected in Table 2.

Yield potential was not available due to the limitation of seeds.

TABLE 1

Summary of Fiber related traits tested in CM1 mutant and it's near iso-genic wild-type line. The seeds were harvested from Aberdeen field in 2009. The value was reported as the dry matter based

| Traits | CM1 | Wild-type |
| --- | --- | --- |
| Beta-glucan | 17.90% | 9.70% |
| Total Fiber | 30.9% | 18.6% |
| Glucomann | 0.28% | 0.16% |
| Water extractable Arabinoxylan | 0.95% | 0.62% |
| Vitamin E (mg/Kg) | 110 | 76 |

TABLE 2

Agronomic data for CM1 and its corresponding wild-type in Aberdeen field, 2011

| Traits | CM1 | Wild-type |
| --- | --- | --- |
| Plant Height | 42 Inch | 42 Inch |
| Heading dates | 180 | 180 |
| 100 seed weight (g) | 3.45 | 4.45 |

Example 2: Deposit Information

Representative of, but not limiting the invention, Applicants have deposited seeds from CM1, with the American Type Culture Collection.

Applicants have made available to the public without restriction a deposit of at least 2500 seeds of a barley plant having ultra-high beta-glucan content i.e., CM1, with the American Type Culture Collection (ATCC), Rockville, Md. 20852. The deposit was made May 17, 2012 and having been assigned ATCC accession No. PTA-12911.

The deposit will be maintained in the ATCC depository, which is a public depository, for a period of 30 years, or 5 years after the most recent request, or for the effective life of the patent, whichever is longer, and will be replaced if a deposit becomes nonviable during that period.

Example 3

The following example illustrates the use of the barley plant having ultra-high beta-glucan content CM1, representative seed having been deposited May 17, 2012 under ATCC Accession No. PTA-12911, as a parent to in a genetic cross to improve the nutritional value of barley lines. The cross produces progeny having ultra-high beta-glucan content as well as other characteristics shared with the parental CM1 line.

Utilization of the CM1 to Improve Barley Nutritional and Other Qualities

As discussed above, CM1 showed very high content of beta-glucan and other dietary fibers. Thus, it is useful for improving the nutritional value of barley by using it as parental line crossing to other barley lines in the breeding procedure.

Crosses we have made include CM1×Tetonia and CM1×Transit. We are currently making more crosses using CM1 as a parent including CM1×winter lines of barley.

Tetonia is a very high yield barley line released from our breeding program in Aberdeen (D. E. Obert et al. Registration of 'Tetonia' Barley Journal of Plant Registrations (2008) Vol. 2 No. 1, p 10-11). Tetonia has low beta-glucan content (about 6% in out tests). This cross combines the high beta-glucan, vitamin E and fibers from CM1 and high yield from Tetonia in the new varieties.

Our experiment in cultivar development using CM1 as parent confirmed the inheritance of the high beta-glucan. We made a cross between CM1 and Tetonia. In the 780 F2 plants of CM1×Tetonia, we identified 180 lines with more than 11.0% of beta-glucan. Among those 180 lines, fifty of them showed 14% or higher beta-glucan contents in grains. Further, there are 85 F3 lines with more than 14% beta-glucan from the cross of CM1×Tetonia. The 180 F2 lines were advanced in head rows and 53 were selected based on beta-glucan contents and field performance. In 2013 Lines were advanced to F5::7 generation. Those 53 lines showed at least 14% BG contents. Those lines will be further evaluated with yield, agronomic traits, and beta-glucan, in multiple years and locations. The best lines will be selected as new food barley cultivars.

Transit is another high beta-glucan line released from our breeding program recently (Obert D E, Hang A, Hu G, Burton C, Saterfield K, Evens C P, Marshall J M, and Jackson E W. 2011. Registration of 'Transit' High β-Glucan Spring Barley. Journal of Plant Registrations 5: 270-272). Cross between CM1 and Transit is expected to use genetic factors contributing to beta-glucan content from traditional high beta-glucan genetic background from transit and a specific mutation from CM1. This cross should have a chance to obtain the best combinations of beta-glucan related genetic factors.

Thirty F5::7 lines from Tetonia×CM1 were evaluated in the Advanced Yield Nursery at Aberdeen, Id. in 2013. Barley lines were planted in 5×10 Ft plot with three replications. Thirteen lines with good yield potential and ultra-high β-Glucan were selected for further tests. The yield potential and β-Glucan data of the 13 lines are summarized.

TABLE 3

Yield and β-Glucan contents of 13 selected F5::7 lines of Tetonia × CM1 from 2013 Aberdeen Field

| Line ID | Yield (Bu/A) | % yield of CM1 | BG % |
|---|---|---|---|
| CM1 | 81 | 100 | 15 |
| 10ARS313-791 | 89 | 110 | 14 |
| 10ARS313-930 | 107 | 129 | 16 |
| 10ARS313-854 | 90 | 111 | 14 |
| 10ARS313-924 | 92 | 114 | 14 |
| 10ARS313-963 | 90 | 111 | 15 |
| 10ARS313-355 | 90 | 111 | 14 |
| 10ARS313-782 | 91 | 112 | 15 |
| 10ARS313-777 | 98 | 121 | 14 |
| 10ARS313-575 | 93 | 115 | 14 |
| 10ARS313-418 | 93 | 115 | 14 |
| 10ARS313-428 | 95 | 117 | 14 |
| 10ARS313-831 | 88 | 109 | 19 |
| 10ARS313-849 | 96 | 119 | 14 |

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A plant or plant part of barley variety CM1 having grain with ultra-high beta-glucan content representative seed of the CM1 variety having been deposited under ATCC accession No. PTA-12911.

2. A seed of the barley plant having grain with ultra-high beta-glucan content of claim 1, wherein the seed produces a barley plant having grain with ultra-high beta-glucan content.

3. A tissue culture of regenerable cells produced from the barley plant of claim 1.

4. A protoplast produced from the tissue culture of claim 3.

5. A barley plant having grain with ultra-high beta-glucan content, regenerated from the tissue culture of claim 3, and wherein said plant has all the physiological and morphological characteristics of the barley variety CM1.

6. A selfed progeny or an F1 hybrid of the plant of claim 1 having grain with ultra-high beta-glucan content and having all the physiological and morphological characteristics of the barley variety CM1.

7. Grain from the barley variety CM1 having grain with ultra-high beta-glucan content representative seed of the variety CM1 having been deposited under ATCC accession No. PTA-12911.

8. A F1 hybrid barley plant wherein at least one parent plant of said hybrid barley plant is the barley variety CM1, said hybrid barley plant having grain with ultra-high beta-glucan content and representative seed of the variety CM1 having been deposited under ATCC accession No. PTA-12911.

9. The hybrid barley plant of claim 8, wherein the parent barley plant CM1 is crossed to a second parent plant, and wherein the second parent plant is "Tetonia" and wherein the hybrid barley plant has grain with ultra-high beta-glucan content.

10. A grain from the hybrid barley plant of claim 8.

* * * * *